United States Patent [19]
Sarin et al.

[11] Patent Number: 5,922,636
[45] Date of Patent: Jul. 13, 1999

[54] CATALYST FOR OLIGOMERIZATION OF ALPHA-OLEFINS

[76] Inventors: Rakesh Sarin, House No. 2204, Sector-9, Faridabad; Sabyasachi Sinha Ray, House No. B-65, Sarita Vihar, New Delhi; Deepak Kumar Tuli, House No. 866, Sector-9, Faridabad; Madan Mohan Rai, House No. 886, Sector-15, Faridabad; Sobhan Ghosh, House No. 188, Sector-14, Faridabad; Akhilesh Kumar Bhatnagar, Gouse No. 205, Sector-7, Faridabad, all of India

[21] Appl. No.: 08/972,951

[22] Filed: Nov. 19, 1997

[51] Int. Cl.$^6$ .............................. B01J 31/02; B01J 31/12; B01J 31/26
[52] U.S. Cl. ................. 502/169; 502/150; 502/152; 502/170; 502/171
[58] Field of Search ...................... 502/150, 152, 502/169, 170, 171

[56] References Cited

U.S. PATENT DOCUMENTS

| | | |
|---|---|---|
| 3,637,503 | 1/1972 | Giannetti et al. . |
| 4,031,159 | 6/1977 | Mandai et al. . |
| 4,107,080 | 8/1978 | Taniyasu et al. . |
| 4,167,534 | 9/1979 | Petrillo et al. . |
| 4,219,691 | 8/1980 | Mandai et al. . |
| 4,268,418 | 5/1981 | Hoff ......................... 502/169 |
| 4,363,746 | 12/1982 | Capshew ................. 502/107 |
| 4,400,565 | 8/1983 | Darden et al. . |
| 4,504,637 | 3/1985 | Shiga et al. ............................. 526/119 |
| 4,629,714 | 12/1986 | Shelly ..................................... 502/113 |
| 5,068,487 | 11/1991 | Theriot . |
| 5,136,118 | 8/1992 | Buchanan et al. . |
| 5,191,140 | 3/1993 | Akatsu et al. . |
| 5,196,635 | 3/1993 | Kumar et al. . |

*Primary Examiner*—Elizabeth D Wood
*Attorney, Agent, or Firm*—Venable; George H. Spencer; Ashley J. Wells

[57] ABSTRACT

A catalyst composition for use in oligomerization of olefins contained in refinery distillate streams including paraffins, naphthenes, and aromatics therein, the catalyst consisting of a first constituent which is at least one aluminum halide; and a second constituent which is at least one alkoxide of a transition metal of Group IVB of the Periodic Table and which has a general formula:

$$M(OR)_4,$$

where M is selected from the group consisting of metals of Group IVB of the Periodic Table and R is one of (a) an alkyl group having from 1–12 carbon atoms or (b) an alkylaryl group having an alkyl chain having from 1–12 carbon atoms.

20 Claims, No Drawings

5,922,636

CATALYST FOR OLIGOMERIZATION OF ALPHA-OLEFINS

BACKGROUND OF THE INVENTION

1. Field of the Invention

This invention relates generally to a novel catalyst composition comprised of an aluminum halide and a metal alkoxide belonging to group IVB, for selectively oligomerizing olefins, present in a mixture of olefins, aromatics, paraffins and cycloparaffins, to polyolefins in good yields. A particular application of the invention is oligomerization of olefins contained in cracked refinery distillate streams to give polyolefins which, after the steps of distillation and stabilization by hydrogenation, give oligomers suitable for use as lubricating oil base stocks.

2. Description of the Related Art

Synthetic oil base stocks having viscosities of about 4 to 30 cSt or above at 100° C. have been prepared in the prior art by oligomerization of olefins by conventional or modified Friedel-Craft catalysts. Thus, by contacting the alpha-olefins with boron trifluoride containing various promoters, synthetic oils suitable for lubricant use have been prepared, such as described in U.S. Pat. Nos. 4,400,565; 5,068,487 and 5,191,140. However, boron trifluoride is a pulmonary irritant and is fast being replaced by less hazardous catalysts like aluminum halides.

A number of aluminum halide catalyst systems have been disclosed for oligomerization of alpha-olefins to poly-alpha-olefins which could be used as lubricating oil base stocks possessing low pour points, higher viscosity index and good oxidation stability. U.S. Pat. No. 3,637,503 discloses the oligomerization of alpha-olefins having from 4 to 16 carbon atoms in the presence of aluminum chloride and a non-polymerizing hydrocarbon diluent. Similarly, aluminum chloride alone or along with organic promoters have been used to oligomerize alpha-olefins either pure alpha-olefins or alpha-olefins in the presence of a non-oligomerizing hydrocarbon diluent, see, for example, U.S. Pat. Nos. 5,196,635; 5,136,118; 4,107,080; 4,219,691 and 4,031,159. It is also known in the related field to oligomerize olefins in which the double bond is statistically distributed along the entire carbon chain. Thus, U.S. Pat. No. 4,167,534 discloses the oligomerization of olefins obtained from a PACOL-OLEX process, by contacting with aluminum chloride to obtain oligomers which, after distillation and catalytic hydrogenation, gave lubricating oil. Even though the feed stock for oligomerization was predominantly olefinic (up to 95%), the yield and the viscosity of the resulting oligomer were very poor.

However, all these processes pertain to oligomerization of either pure alpha-olefins or mixtures of pure alpha-olefins and, surprisingly, there are no reports on the utilization of linear olefins contained in refinery streams for the production of synthetic lubricant base stocks. Various refinery produced cracked distillate streams, particularly from Coker and FCC units, are quite rich in desired alpha-olefins which can be selectively concentrated by the process of urea adduction.

A major deficiency of the conventional Friedel-Craft catalysts is their inability to selectively oligomerize olefins in the presence of other unsaturated compounds like aromatics. However, aluminum chloride alone or with promoters is known to promote the alkylation of aromatics with olefins when applied to cracked refinery distillate streams which contained appreciable amounts of aromatics along with olefins. The oligomeric product thus obtained contain alkylated aromatics which made these products unsuitable for use as lubricating oils because of very poor oxidation stability. No prior art method either discloses or teaches any catalyst system which can selectively oligomerize olefins to polyolefins in the presence of aromatics. Consequently, it is in fact impossible to prepare an olefin oligomer having high viscosity index and high oxidation stability which could be qualified for such uses as gas turbine oil, hydraulic fluid for aircraft, crankcase oils, etc. by selective oligomerization of olefins present in the cracked refinery stream distillates which also contain aromatics, besides paraffins and cycloparaffins, by use of Friedel-Craft catalyst systems disclosed in the prior art. The present invention provides for a catalyst composition for preparation of olefin oligomers suitable for use as lubricating oils by selective oligomerization of olefins, contained in cracked refinery stream distillates, which have been processed through a step of urea adduction.

An object of the present invention is to propose a catalyst composition for selectively oligomerizing olefins present in cracked refinery stream distillates which are comprised of olefins, aromatics, paraffins and cycloparaffins having 8 to 20 carbon atoms.

A further object of this invention is to propose a catalyst composition which provides higher conversion of olefins present in the cracked refinery stream distillates, processed through a step of urea adduction and containing up to 5% aromatics.

Yet another object of the present invention is to propose a catalyst system for selective oligomerization of olefins contained in refinery distillate streams to produce oligomers having high viscosity index, low pour point and higher oxidation stability for use as base stocks in synthetic lubricants.

SUMMARY OF THE INVENTION

According to this invention, there is provided a catalyst composition for use in oligomerization of olefins contained in refinery distillate streams comprising an aluminum halide component and a catalyst component selected from an alkoxide of a metal belonging to group IVB.

Further according to this invention, there is provided a process for preparing poly-alpha-olefin synthetic lubricants comprising oligomerization of olefins of cracked refinery streams having 8 to 20 carbon atoms in the presence of corresponding paraffins, naphthenes and aromatics, and in the presence of a catalyst consisting of an aluminum halide and group IVB transition metal alkoxide, to provide an olefin oligomer having a viscosity of 7–30 cSt at 100° C.

The catalyst composition used in the oligomerization process of the present invention is a two component system comprising (A) an aluminum halide component and (B) a second catalyst component which is an alkoxide of a metal belonging to group IV B. The aluminum halides which are suitable for use in the catalyst system of the present invention include aluminum fluoride, aluminum chloride, aluminum bromide and aluminum iodide and mixtures thereof. The preferred aluminum halide is aluminum chloride. The second component of the proposed oligomerization catalyst system comprises a metal alkoxide having the general formula $M(OR)_4$, wherein M is selected from the group of metals belonging to group IVB of the periodic table and R is an alkyl group of 1 to 12 carbon atoms or an alkylaryl having an alkyl chain of 1–12 carbon atoms. Preferably R is a lower alkyl of 2 to 6 carbon atoms.

A preferred catalyst composition is obtained when the metal alkoxide is a titanium alkoxide. A particularily preferred catalyst composition contains aluminum chloride and a titanium alkoxide such as titanium tetra-isopropoxide or titanium tetra-n-butoxide.

The molar ratio of aluminum halide to the transition metal alkoxide is important for optimum catalyst activity and for product quality in terms of viscosity and pour points. Generally the molar ratio of aluminum to transition metal is from 100:1 to 4:1, preferably about 60:1 to 10:1. The amount of aluminum-halide catalyst can vary and amounts of from about 0.5 to 10 weight percent based on the amount of olefin is preferred. The specially preferred amount of aluminum halide is from 1 to 4 weight percent based on the amount of olefins.

The raw material suitable for the present catalyst composition can consist of alpha-olefins having a number of carbon atoms between 8 and 24, n-olefins having the double bond statistically distributed along the entire carbon chain and having a number of carbon atoms between 8 and 24, and the mixtures of n-olefins and alpha-olefins in any ratio. The proposed catalyst composition is also suitable for raw materials obtained from the PACOL process or from wax cracking and containing a mixture of olefins and paraffins and having a number of carbon atoms between 8 and 24. Yet another raw material suitable for the present catalyst composition is the cracked refinery distillate cuts, i.e., distillate cuts from FCC or coker units. These cuts were mixtures of olefins, aromatics, paraffins and cycloparaffins having a number of carbon atoms between 8 and 24.

A preferred feed for oligomerization with the catalyst composition of the present invention is that obtained through the process of urea adduction of cracked refinery distillate streams. Methods are generally known in the prior art to obtain linear olefins and linear paraffins mixtures by urea adduction of cracked refinery distillate streams, viz., naphtha, kerosene, diesel and gas oil. See, for example, A.Hoope, in "Advances in Petroleum Chemistry and Refining", Vol. 8, Ed., Kobe-McKetta, Inter-Science Publication, New York, 1964, which is incorporated by reference. However the urea adducted olefin rich feed is generally contaminated with 0.1–5.0% aromatics, depending upon the process conditions. Surprisingly, it was found that the catalyst composition of the present invention results in selective oligomerization of olefins contained in the cracked refinery distillate streams processed through the step of urea adduction.

The olefins are oligomerized in contact with the present catalyst composition under conventional oligomerization conditions. Oligomerization is conducted at temperatures ranging from 30–200° C., preferentially from about 70 to 120° C. The reactions can either be conducted under reflux conditions or in an autoclave under autogeneous pressure. For effecting the oligomerization of olefins by the catalyst composition of the present invention, the appropriate amount of aluminum halide and transition metal alkoxide are premixed in the presence of an inert non-polymerizing solvent (i.e., n-heptane, n-octane etc.) and the resulting mixture added slowly to the olefinic feed stock. However, no difference was observed even by dissolving the transition metal alkoxide in the olefinic feed stock and subsequent stepwise addition of aluminum halide to this mixture or vice versa. Lower reaction temperatures were generally associated with enhancement in the viscosity of the oligomer and a decrease in the overall yield. The reaction is normally carried out over a period of about 1 to 12 hours, preferably for about 1 to 4 hours.

The regulation of the molecular weight of the oligomers produced and hence other physical characteristics like viscosity, viscosity index and pour point, can be controlled during the oligomerization by changing the ratio of aluminum halide to metal alkoxide, by variation in reaction temperature and by variation in reaction duration. After completing the oligomerization reaction, the product is passed through a column of silica/alumina to remove the residual catalyst, and then subjected to distillation under reduced pressure to remove unoligomerised products and olefin dimers. To further improve the oxidation stability and/or thermal stability of the product, it can be subjected to hydrogenation treatment by use of typical hydrogenation catalysts, such as Raney nickel, nickel on Kieselguhr or Pd on charcoal. At present, the reaction mechanism of the complex of aluminum halide with transition metal alkoxide which is responsible for the selective oligomerization of olefins in the presence of other unsaturated compounds like aromatics is yet to be clarified. However, it is likely that oligomer chain growth occurs as a result of olefin coordination on a transition metal which has unoccupied co-ordination sites. Subsequently, olefin insertion can take place into a transition metal carbon bond to give oligomeric chain growth. However, the bulky aromatics are not able to make transition metal-carbon bonds and hence are excluded in the chain growth step. Finally the chain transfer can occur as a result of P-hydrogen elimination from the oligomeric chain attached to the transition metal and the catalytic center, namely, the transition metal-carbon bond is restored again.

As will be understood from the foregoing elucidation, according to the oligomerization catalyst composition of the present invention it is possible to selectively oligomerize olefins in the presence of aromatics, to get the oligomer oil. These oligomers can be tailor made to a viscosity range of 7 to 30 cSt at 100° C. by variation effected in the catalyst composition and by process parameters. After stabilization by hydrogenation, these oligomers show high viscosity index, low pour points, excellent thermal/oxidation stability and can be used as synthetic lubricant base stock.

DESCRIPTION OF THE PREFERRED EMBODIMENTS

The present invention will be further illustrated by, but by no means is limited to, the following examples. In the following examples, the kinematic viscosity was determined in the manner described in ASTM-D-45, the viscosity index was determined in the manner described in ASTM-D-2270, and the pour point was determined in the manner described in ASTM-D-97. The detection of aromatics in the feed stock and oligomeric oil was carried out by NMR spectroscopy.

EXAMPLE 1

The reaction was carried out in a 1 liter four necked round bottom flask, fitted with a mechanical stirrer, a solid addition funnel, a thermometer and a gas purging tube. The system was kept under a positive pressure of dry nitrogen and 2% of anhydrous aluminum chloride and 0.2% titanium isopropoxide were added. Keeping the Al/Ti ratio equal to 21, 500 g of 1-decene was dropwise added to the mixture over a period of 1 hour. The temperature of this stirred mixture was raised to 100° C. and oligomerization was carried out for a period of 2 hours. After completion of reaction, the product mixture was filtered through a bed of silica to remove the deactivated catalyst. The filtrate was subjected to flushing at 160° C./0.5 mm Hg to remove unreacted decene and its dimers, to obtain the oligomerized oil. The performance evaluation of products obtained is described in Tables 1 and 2.

EXAMPLE 2

In an experimental set up similar to the one as described for Example 1, 2% aluminum chloride and 0.05% Ti(Obu)4 were mixed together and reacted with 1-decene. The oligomerization reaction was carried out at 80/100° C. and oligomeric product was isolated as described in Example 1. The results are reported in Tables 1 and 2.

EXAMPLE 3

The reaction was carried out as described for Example I and using the identical catalyst composition except that the oligomerization feed stock was a Pacol product cut comprised of $C_{10}$ to $C_{14}$ olefin-paraffin mixture having 15% olefins. Some typical results are described in Tables 1 and 2.

EXAMPLE 4

The reaction was carried out as described for Example 1 and using the identical catalyst composition except that the oligomerization feed stock was a cracked refinery stream cut having a boiling range of 180–220° C., and being comprised of linear $C_{10}$ to $C_{14}$ hydrocarbons, having 32% olefins, 44% paraffins, 20% naphthenes and 4% aromatics. Some typical results are described in Tables 1 and 2.

EXAMPLE 5

The reaction was earned out as described for Example 1, and using the identical catalyst composition, except that the oligomenzation feed stock was a cracked refinery stream cut, processed through the step of urea adduction, having boiling range of 180–220° C., comprised of linear $C_{10}$ to $C_{14}$ hydrocarbons, having 29% olefins, 68% paraffins and 3% aromatics. Some typical results are described in Tables 1 and 2.

TABLE 1

PERFORMANCE EVALUATION OF SYNTHESIZED OLIGOMERS

| EXAMPLE NO. | CONVERSION (%)** | KV,cSt (100° C.) | VI | POUR POINT (° C.) |
|---|---|---|---|---|
| 1 | 97 | 22.1 | 140 | −27 |
| 2 | 98 | 12.3 | 132 | −30 |
| 3 | 94 | 26.5 | 134 | −27 |
| 4 | 93 | 20.4 | 142 | −30 |
| 5 | 95 | 20.9 | 138 | −30 |

**CONVERSION BASED ON OLEFIN CONTENT

TABLE 2

IP-48 OXIDATION TEST RESULTS ON SYNTHESIZED OLIGOMERS AFTER HYDROGENATION

| Example No. | Kinematic Viscosity at 100° C. | | CCR (%) | | TAN (mg KOH/g) | |
|---|---|---|---|---|---|---|
| | Before Test | After Test | Before Test | After Test | Before Test | After Test |
| 1 | 22.1 | 30.9 | 0.01 | 0.13 | 0.15 | 6.4 |
| 2 | 12.3 | 17.6 | 0.01 | 0.12 | 0.17 | 6.8 |
| 3 | 26.5 | 36.8 | 0.01 | 0.17 | 0.13 | 8.3 |
| 4 | 20.4 | 29.8 | 0.01 | 0.14 | 0.15 | 8.7 |
| 5 | 20.9 | 30.5 | 0.01 | 0.15 | 0.16 | 7.9 |

We claim:

1. A catalyst composition for use in oligomerization of olefins contained in refinery distillate streams including paraffins, naphthenes, and aromatics therein, the catalyst consisting of a first constituent which is at least one aluminum halide; and a second constituent which is at least one alkoxide of a transition metal of Group IVB of the Periodic Table and which has a general formula:

$$M(OR)_4,$$

where M is selected from the group consisting of metals of Group IVB of the Periodic Table and R is one of (a) an alkyl group having from 1–12 carbon atoms or (b) an alkylaryl group having an alkyl chain having from 1–12 carbon atoms.

2. The catalyst composition as claimed in claim 1, wherein the at least one aluminum halide is selected from the group consisting of aluminum chloride, aluminum bromide, aluminum iodide and mixtures thereof.

3. The catalyst composition as claimed in claim 1, wherein the alkylaryl group has an alkyl chain having from 2–6 carbon atoms.

4. The catalyst composition as claimed in claim 1, wherein the transition metal is titanium, and wherein the at least one alkoxide is titanium alkoxide.

5. The catalyst composition as claimed in claim 1, wherein the catalyst composition has a molar ratio of aluminum to transition metal which ranges from 100:1 to 4:1.

6. The catalyst composition as claimed in claim 5, wherein the catalyst composition has a molar ratio of aluminum to transition metal which ranges from 60:1 to 10:1.

7. A catalyst composition for use in oligomerization of olefins contained in refinery distillate streams including paraffins, naphthenes, and aromatics therein, the catalyst consisting of a first constituent which is at least one aluminum halide; and a second constituent which is at least one alkoxide of a transition metal of Group IVB of the Periodic Table and which has a general formula:

$$M(OR)_4,$$

where M is selected from the group consisting of metals of Group IVB of the Periodic Table and R is one of (a) an alkyl group having from 1–12 carbon atoms or (b) an alkylaryl group having an alkyl chain having from 1–12 carbon atoms, wherein the catalyst composition has a molar ratio of aluminum to transition metal which ranges from 100:1 to 4:1.

8. The catalyst composition as claimed in claim 7, wherein the at least one aluminum halide is selected from the group consisting of aluminum chloride, aluminum bromide, aluminum iodide and mixtures thereof.

9. The catalyst composition as claimed in claim 8, wherein the transition metal is titanium, and wherein the at least one alkoxide is titanium alkoxide.

10. The catalyst composition as claimed in claim 9, wherein the at least one aluminum halide is aluminum chloride.

11. The catalyst composition as claimed in claim 10, wherein the titanium alkoxide is selected from the group consisting of titanium tetra-iso-propoxide and titanium tetra-n-butoxide.

12. The catalyst composition as claimed in claim 7, wherein the catalyst composition has a molar ratio of aluminum to transition metal which ranges from 60:1 to 10:1.

13. The catalyst composition as claimed in claim 7, wherein the alkylaryl group has an alkyl chain having from 2–6 carbon atoms.

14. The catalyst composition as claimed in claim 7, wherein the transition metal is titanium, and wherein the at least one alkoxide is titanium alkoxide.

15. A catalyst composition for use in oligomerization of olefins contained in refinery distillate streams including paraffins, naphthenes, and aromatics therein, the catalyst consisting of a first constituent which is at least one aluminum halide; and a second constituent which is at least one titanium alkoxide and which has a general formula:

$$Ti(OR)_4,$$

where R is one of (a) an alkyl group having from 1–12 carbon atoms or (b) an alkylaryl group having an alkyl chain having from 1–12 carbon atoms.

16. The catalyst composition as claimed in claim 15, wherein the at least one aluminum halide is aluminum chloride.

17. The catalyst composition as claimed in claim 16, wherein the titanium alkoxide is selected from the group consisting of titanium tetra-iso-propoxide and titanium tetra-n-butoxide.

18. The catalyst composition as claimed in claim 15, wherein the catalyst composition has a molar ratio of aluminum to transition metal which ranges from 100:1 to 4:1.

19. The catalyst composition as claimed in claim 18, wherein the catalyst composition has a molar ratio of aluminum to transition metal which ranges from 60:1 to 10:1.

20. The catalyst composition as claimed in claim 15, wherein the alkylaryl group has an alkyl chain having from 2–6 carbon atoms.

* * * * *